(12) United States Patent
Parker et al.

(10) Patent No.: US 8,173,835 B2
(45) Date of Patent: *May 8, 2012

(54) METHOD AND APPARATUS FOR DRYING CARBOXYLIC ACID

(75) Inventors: Kenny Randolph Parker, Afton, TN (US); Philip Edward Gibson, Kingsport, TN (US)

(73) Assignee: Grupo Petrotemex, S.A. DE C.V., San Pedro Garza Garcia (MX)

( * ) Notice: Subject to any disclaimer, the term of this patent is extended or adjusted under 35 U.S.C. 154(b) by 917 days.

This patent is subject to a terminal disclaimer.

(21) Appl. No.: 11/701,128

(22) Filed: Feb. 1, 2007

(65) Prior Publication Data

US 2007/0204479 A1  Sep. 6, 2007

Related U.S. Application Data

(60) Provisional application No. 60/777,906, filed on Mar. 1, 2006, provisional application No. 60/777,908, filed on Mar. 1, 2006.

(51) Int. Cl.
*C07C 51/61* (2006.01)

(52) U.S. Cl. ........ 562/416; 562/405; 562/407; 562/408; 562/409; 562/412

(58) Field of Classification Search .................. None
See application file for complete search history.

(56) References Cited

U.S. PATENT DOCUMENTS

| | | |
|---|---|---|
| 3,152,947 A | 10/1964 | Monick et al. |
| 3,425,135 A | 2/1969 | Langsetmo et al. |
| 3,943,233 A | 3/1976 | Swanson et al. |
| 4,158,738 A | 6/1979 | Scott et al. |
| 4,161,578 A | 7/1979 | Herron |
| 4,219,669 A | 8/1980 | Tsuchiya et al. |
| 4,268,972 A | 5/1981 | Molls et al. |
| 4,330,676 A | 5/1982 | Moxham |
| 4,356,319 A | 10/1982 | Roffia et al. |
| 4,495,070 A | 1/1985 | Pierson |
| 4,589,215 A | 5/1986 | Iwasaki et al. |
| 4,658,891 A | 4/1987 | Wurtz |
| 4,769,489 A | 9/1988 | Abrams et al. |
| 4,792,621 A | 12/1988 | Abrams |
| 4,894,117 A | 1/1990 | Bianchi et al. |
| 4,914,230 A | 4/1990 | Abrams et al. |
| 4,939,297 A | 7/1990 | Browder et al. |
| 5,043,007 A | 8/1991 | Davis |
| 5,100,510 A | 3/1992 | Bianchi et al. |
| 5,175,355 A | 12/1992 | Streich |
| 5,200,557 A | 4/1993 | Gee et al. |
| 5,271,163 A | 12/1993 | Pikus et al. |
| 5,563,293 A | 10/1996 | Hindmarsh et al. |
| 5,583,254 A | 12/1996 | Turner |
| 5,643,468 A | 7/1997 | Ure |
| 5,676,847 A | 10/1997 | Yamamoto |
| 5,698,734 A | 12/1997 | Turner et al. |
| 5,705,682 A | 1/1998 | Ohkoshi et al. |
| 5,767,311 A | 6/1998 | Lee et al. |
| 5,770,765 A | 6/1998 | Ohkoshi |
| 5,840,965 A | 11/1998 | Turner et al. |
| 5,840,968 A | 11/1998 | Lee et al. |
| 5,877,271 A | 3/1999 | Billovits et al. |
| 5,877,346 A | 3/1999 | Hindmarsh et al. |
| 5,973,196 A | 10/1999 | Takano et al. |
| 6,013,835 A | 1/2000 | Lee et al. |
| 6,031,128 A | 2/2000 | Roh et al. |
| 6,054,610 A | 4/2000 | Lee et al. |
| 6,113,866 A | 9/2000 | Lee et al. |
| 6,143,926 A | 11/2000 | Parten |
| 6,150,553 A | 11/2000 | Parten |
| 6,153,790 A | 11/2000 | June et al. |
| 6,245,939 B1 | 6/2001 | Hsu et al. |
| 6,307,099 B1 | 10/2001 | Turner et al. |
| 6,310,239 B1 | 10/2001 | Roh et al. |
| 6,562,997 B2 | 5/2003 | Sikkenga et al. |
| 6,580,005 B1 | 6/2003 | Yazaki et al. |
| 6,620,966 B2 | 9/2003 | Ohkoshi et al. |
| 6,639,104 B2 | 10/2003 | Piras et al. |
| 6,655,531 B1 | 12/2003 | Beard et al. |
| 6,765,113 B2 | 7/2004 | Graham et al. |
| 7,074,954 B2 | 7/2006 | Sheppard et al. |
| 7,132,566 B2 | 11/2006 | Sumner, Jr. et al. |
| 2002/0016500 A1 | 2/2002 | Matsumoto et al. |
| 2002/0193630 A1 | 12/2002 | Lin et al. |
| 2003/0004372 A1 | 1/2003 | Piras et al. |
| 2003/0004373 A1 | 1/2003 | Piras et al. |
| 2003/0059516 A1 | 3/2003 | Brubacher et al. |
| 2004/0098877 A1 | 5/2004 | Stock et al. |
| 2004/0142079 A1 | 7/2004 | Brubacher et al. |
| 2004/0191139 A1 | 9/2004 | Numata et al. |
| 2004/0244536 A1 | 12/2004 | Lin |
| 2004/0245176 A1 | 12/2004 | Parker et al. |
| 2004/0249208 A1 | 12/2004 | Lin et al. |
| 2005/0000108 A1* | 1/2005 | Ragnarsson ....................... 34/92 |
| 2005/0159616 A1* | 7/2005 | Parker et al. .................. 562/485 |
| 2005/0159617 A1 | 7/2005 | Parker et al. |
| 2005/0228164 A1 | 10/2005 | Lin et al. |
| 2006/0047165 A1 | 3/2006 | Lin et al. |

FOREIGN PATENT DOCUMENTS

| | | |
|---|---|---|
| EP | 0 858 990 A1 | 8/1998 |
| EP | 1 402 942 A1 | 3/2004 |
| GB | 1 470 574 | 4/1977 |

OTHER PUBLICATIONS

USPTO Office Action dated Feb. 3, 2009 for copending U.S. Appl. No. 11/709,464. Copending U.S. Appl. No. 11/701,129, filed Feb. 1, 2007, Kenny Randolph Parker et al.

Copending U.S. Appl. No. 11/709,464, filed Feb. 22, 2007, Kenny Randolph Parker et al.

Brochure entitled "A Turn for the Better in Thermal Processing," by Bepex Corporation, 1992 Bepex.

*Primary Examiner* — Sudhakar Katakam

(74) *Attorney, Agent, or Firm* — Oblon, Spivak, McClelland, Maier & Neustadt, L.L.P.

(57) ABSTRACT

Disclosed is a method and apparatus for drying a wet cake in a carboxylic acid production process. The method comprises employing a contact dryer for drying solid particles of carboxylic acid, where the solid particles can have a residence time of less than about 7 minutes in the dryer and an exit temperature of less than about 250° C. upon exiting the dryer.

56 Claims, 3 Drawing Sheets

OTHER PUBLICATIONS

Brochure entitled "Thermal Processing—Beyond the Basics," by Bepex International LLC, 2005 Bepex.

Article entitled "Solidaire," by Bepex International LLC, retrieved from the internet at http://www.bepex.com/torusdisc.htm, on Nov. 12, 2009.

Article entitled "Torusdisc—Single or Twin Rotor Dryer," by Bepex International LLC, retrieved from the internet at http://www.bepex.com/torusdisc.htm, on Nov. 12, 2009.

USPTO Office Action dated Sep. 28, 2009, in copending U.S. Appl. No. 11/709,464.

USPTO Office Action dated Jul. 7, 2009 in copending U.S. Appl. No. 11/709,464.

USPTO Office Action dated Mar. 9, 2010 in copending U.S. Appl. No. 11/701,129.

* cited by examiner

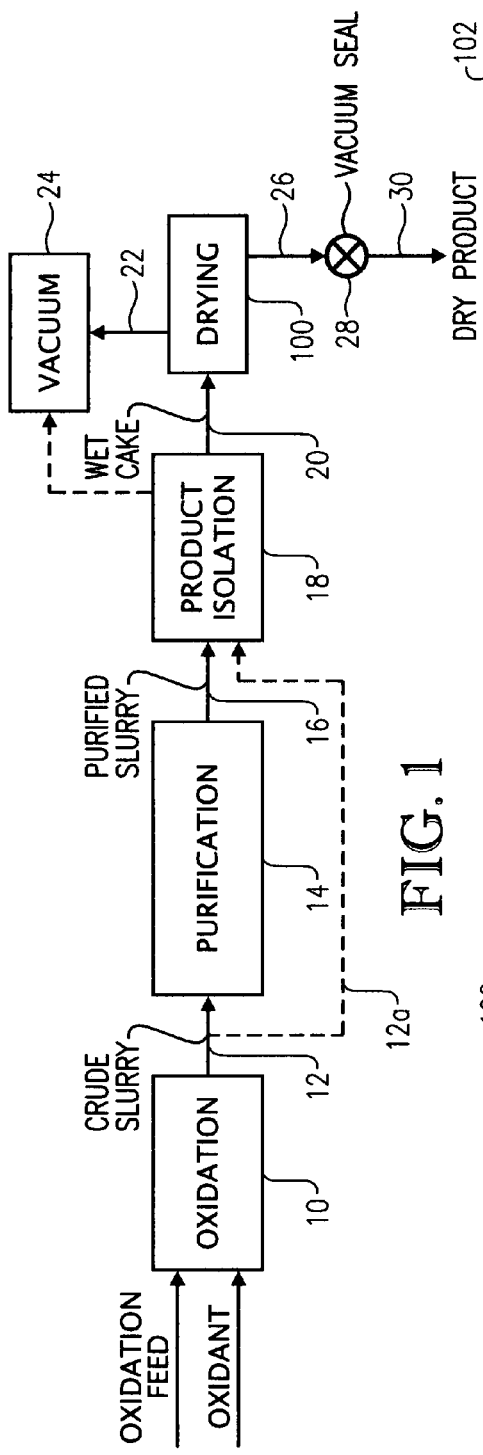
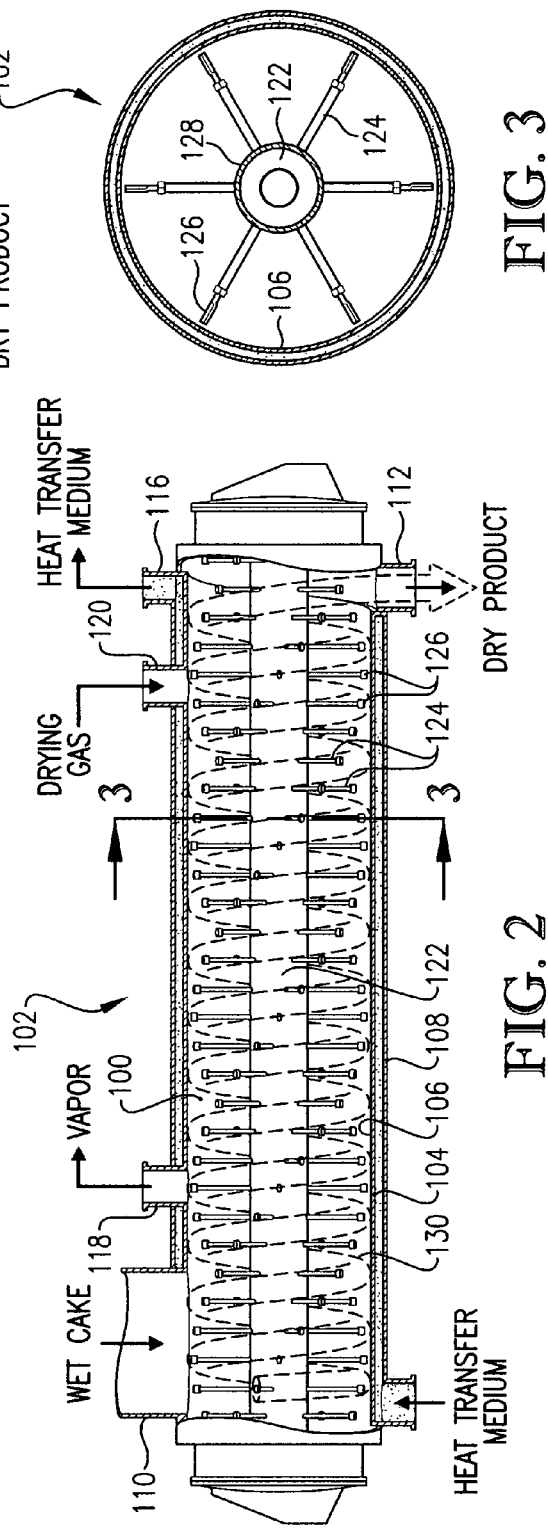

US 8,173,835 B2

METHOD AND APPARATUS FOR DRYING CARBOXYLIC ACID

RELATED APPLICATIONS

This application claims the priority benefit of U.S. Provisional Pat. App. Ser. Nos. 60/777,906 and 60/777,908, both filed Mar. 1, 2006, the entire disclosures of which are incorporated herein by reference.

BACKGROUND OF THE INVENTION

1. Field of the Invention

The present invention relates generally to a drying process for use in the production of a carboxylic acid. More specifically, the present invention concerns a method for drying solid particles of terephthalic acid in a drying zone where the residence time of the solid particles in the drying zone is reduced and the exit temperature of the solid particles is less than about 250° C.

2. Description of the Prior Art

In conventional crude terephthalic acid (CTA) production processes, para-xylene undergoes oxidation to form CTA particles. The CTA particles are then typically subjected to isolation and washing. In a conventional purified terephthalic acid (PTA) production process, an additional step is employed where the CTA particles are purified prior to the isolation/washing step. In either a CTA or a PTA production process, the terephthalic acid (TPA) particles exiting the isolation/washing step are typically in the form of a wet cake. In some TPA production processes, the wet cake is then dried in a dryer to thereby produce a substantially dry TPA product.

Various methods are known in the art for drying a TPA product. Such methods include the use of a rotary dryer, as well as drying the TPA wet cake by contacting it with a flow of inert gas, which can be achieved in a fluid bed dryer, a ring dryer, or in a solids conveying system. However, conventional methods for drying TPA can cause significant product degradation and/or sublimation, both of which are undesirable. Accordingly, there is a need for methods and/or equipment that can minimize product degradation and/or sublimation when drying a TPA product.

SUMMARY OF THE INVENTION

One embodiment of the present invention concerns a method for drying solid particles comprising a carboxylic acid. The method of this embodiment comprises: (a) introducing a wet cake comprising the solid particles into a contact dryer comprising an inner surface; and (b) drying the wet cake in the contact dryer to thereby produce a substantially dry product comprising at least a portion of the solid particles, wherein at least about 10 percent of the solid particles form a layer over at least a portion of the inner surface, wherein the layer has an average thickness of less than about 1.5 inches, wherein the solid particles have an exit temperature of less than about 250° C. upon exiting the dryer.

Another embodiment of the present invention concerns a method for producing a substantially dry crude terephthalic acid (CTA) particulate product. The method of this embodiment comprises: (a) oxidizing an aromatic compound in an oxidation zone to thereby produce a slurry comprising solid CTA particles; (b) treating at least a portion of the slurry in a product isolation zone to thereby produce a wet cake comprising at least a portion of the solid CTA particles; and (c) drying at least a portion of the wet cake in a contact dryer comprising an inner surface to thereby produce the substantially dry CTA particulate product, wherein at least about 10 percent of the solid CTA particles form a layer over at least a portion of the inner surface, wherein the layer has an average thickness of less than about 1.5 inches, wherein the solid CTA particles have an exit temperature of less than about 250° C. upon exiting the dryer.

Yet another embodiment of the present invention concerns a method for drying a wet cake comprising terephthalic acid (TPA). The method of this embodiment comprises: (a) introducing the wet cake into a contact dryer; and (b) drying the wet cake in the dryer to thereby produce a dry TPA product, wherein, during drying, at least a portion of the TPA in the wet cake forms a thin layer on the inside surface of the dryer, wherein the dry TPA product has a temperature in the range of from about 105 to about 240° C. upon exiting the dryer.

BRIEF DESCRIPTION OF THE DRAWING FIGURES

A preferred embodiment of the present invention is described in detail below with reference to the attached drawing figures, wherein:

FIG. 1 is a process flow diagram illustrating a system for the production, purification, and drying of carboxylic acid constructed in accordance with the present invention, particularly illustrating a configuration where the crude slurry from the oxidation reactor is subjected to purification, the resulting purified slurry is subjected to product isolation, and the wet cake from the product isolation zone is subjected to drying in a drying zone;

FIG. 2 is a side view of a dryer that may be used in one embodiment of the present invention with certain sections being cut away to more clearly illustrate the operation of the dryer;

FIG. 3 is a sectional view of the dryer taken along line 3-3 in FIG. 2, particularly illustrating a rotor having a plurality of radial arms affixed thereto and paddles attached to each individual radial arm;

Figure 4:
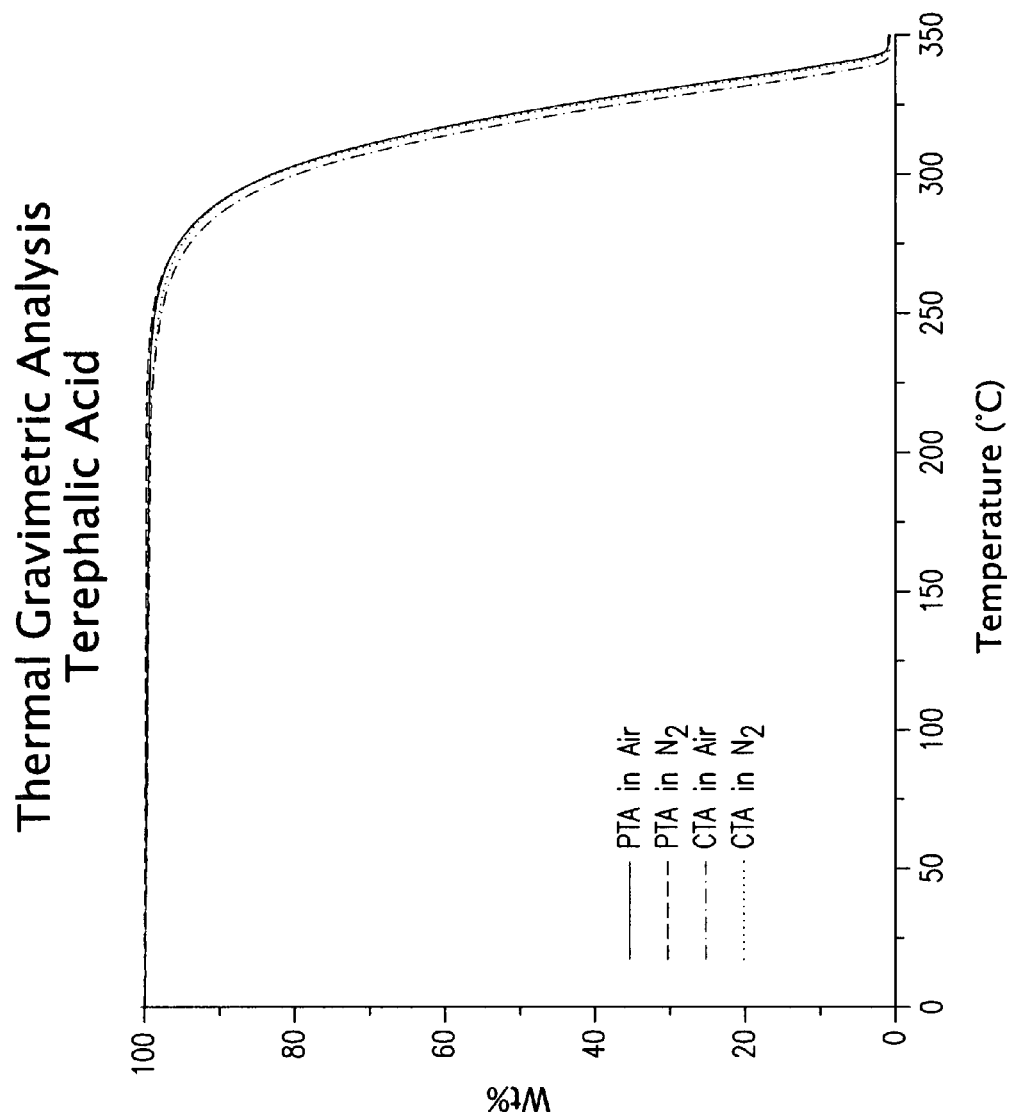
Figure 4A:
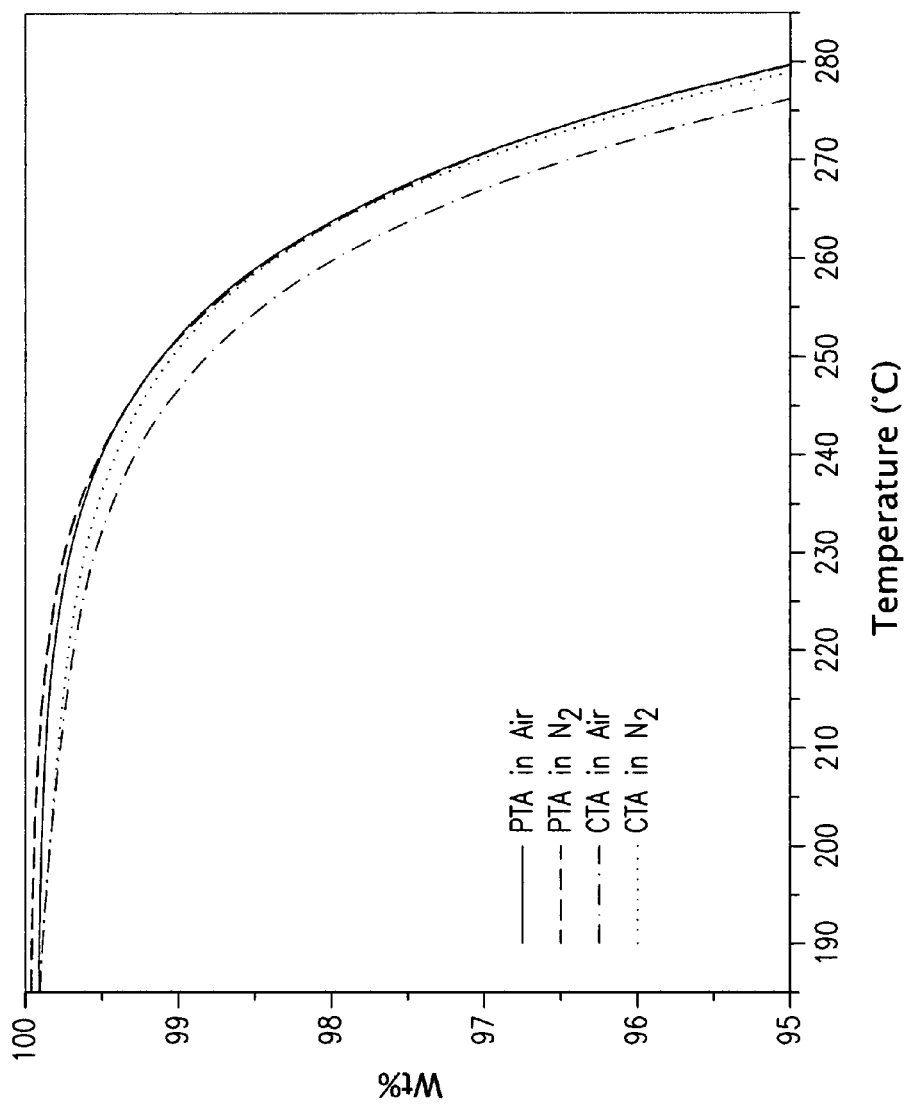

FIG. 4 is a weight percent vs. time plot depicting the thermal gravimetric analyses of purified terephthalic acid (PTA) in air, PTA in nitrogen, crude terephthalic acid (CTA) in air, and CTA in nitrogen, determined in accordance with the procedure described in Example 5; and FIG. 4a is a magnified view of the plot depicted in FIG. 4, particularly illustrating the weight percent range from 95 to 100 and the time range from 185 to 285 of the weight percent vs. time plot depicted in FIG. 4.

DETAILED DESCRIPTION

FIG. 1 illustrates an embodiment of the present invention where carboxylic acid produced in an oxidation reactor and purified in a purification reactor is subjected to product isolation. A portion of the resulting wet cake from the product isolation zone is treated in a drying zone to thereby produce a substantially dry carboxylic acid particulate product. Various embodiments of the drying zone are described in more detail below with reference to FIGS. 2 and 3.

In the embodiment illustrated in FIG. 1, a predominately fluid-phase feed stream containing an oxidizable compound (e.g., para-xylene), a solvent (e.g., acetic acid and/or water), and a catalyst system (e.g., cobalt, manganese, and/or bromine) can be introduced into oxidation zone 10. A predominately gas-phase oxidant stream containing molecular oxygen can also be introduced into oxidation zone 10. The fluid- and gas-phase feed streams form a multi-phase reaction medium in oxidation zone 10. The oxidizable compound can undergo partial oxidation in a liquid phase of the reaction medium contained in oxidation zone 10.

In one embodiment of the present invention, oxidation zone 10 can comprise an agitated reactor. Agitation of the reaction medium in oxidation zone 10 can be provided by any means known in the art. As used herein, the term "agitation" shall denote work dissipated into the reaction medium causing fluid flow and/or mixing. In one embodiment, oxidation zone 10 can be a mechanically-agitated reactor equipped with means for mechanically agitating the reaction medium. As used herein, the term "mechanical agitation" shall denote agitation of the reaction medium caused by physical movement of a rigid or flexible element(s) against or within the reaction medium. For example, mechanical agitation can be provided by rotation, oscillation, and/or vibration of internal stirrers, paddles, vibrators, or acoustical diaphragms located in the reaction medium. In another embodiment of the present invention, oxidation zone 10 can comprise a bubble column reactor. As used herein, the term "bubble column reactor" shall denote a reactor for facilitating chemical reactions in a multi-phase reaction medium, wherein agitation of the reaction medium is provided primarily by the upward movement of gas bubbles through the reaction medium. As used herein, the terms "majority," "primarily," and "predominately" shall mean more than 50 percent.

The oxidizable compound present in the fluid-phase feed stream introduced into oxidation zone 10 can comprise at least one hydrocarbyl group. Also, the oxidizable compound can comprise an aromatic compound. In one embodiment, the oxidizable compound can comprise an aromatic compound with at least one attached hydrocarbyl group or at least one attached substituted hydrocarbyl group or at least one attached heteroatom or at least one attached carboxylic acid function (—COOH). In another embodiment, the oxidizable compound can comprise an aromatic compound with at least one attached hydrocarbyl group or at least one attached substituted hydrocarbyl group with each attached group comprising from 1 to 5 carbon atoms. In yet another embodiment, the oxidizable compound can be an aromatic compound having exactly two attached groups with each attached group comprising exactly one carbon atom and consisting of methyl groups and/or substituted methyl groups and/or at most one carboxylic acid group. Suitable examples of the oxidizable compound include, but are not limited to, para-xylene, meta-xylene, para-tolualdehyde, meta-tolualdehyde, para-toluic acid, meta-toluic acid, and/or acetaldehyde. In one embodiment of the present invention, the oxidizable compound comprises para-xylene.

A "hydrocarbyl group," as defined herein, is at least one carbon atom that is bonded only to hydrogen atoms and/or to other carbon atoms. A "substituted hydrocarbyl group," as defined herein, is at least one carbon atom bonded to at least one heteroatom and to at least one hydrogen atom. "Heteroatoms," as defined herein, are all atoms other than carbon and hydrogen atoms. "Aromatic compounds," as defined herein, comprise an aromatic ring and can comprise at least 6 carbon atoms and can also comprise only carbon atoms as part of the ring. Suitable examples of such aromatic rings include, but are not limited to, benzene, biphenyl, terphenyl, naphthalene, and other carbon-based fused aromatic rings.

The amount of oxidizable compound present in the fluid-phase feed stream introduced into oxidation zone 10 can be in the range of from about 4 to about 20 weight percent, or in the range of from 6 to 15 weight percent.

The solvent present in the fluid-phase feed stream introduced into primary oxidation reactor 10 can comprise an acid component and a water component. The solvent can be present in the fluid-phase feed stream at a concentration in the range of from about 60 to about 98 weight percent, in the range of from about 80 to about 96 weight percent, or in the range of from 85 to 94 weight percent. The acid component of the solvent can be an organic low molecular weight monocarboxylic acid having from 1 to 6 carbon atoms, or 2 carbon atoms. In one embodiment, the acid component of the solvent can comprise acetic acid. The acid component can make up at least about 75 weight percent of the solvent, at least about 80 weight percent of the solvent, or in the range of from 85 to 98 weight percent of the solvent, with the balance being water.

As mentioned above, the fluid-phase feed stream introduced into oxidation zone 10 can also include a catalyst system. The catalyst system can be a homogeneous, liquid-phase catalyst system capable of promoting at least partial oxidation of the oxidizable compound. Also, the catalyst system can comprise at least one multivalent transition metal. In one embodiment, the catalyst system can comprise cobalt, bromine, and/or manganese.

When cobalt is present in the catalyst system, the fluid-phase feed stream can comprise cobalt in an amount such that the concentration of cobalt in the liquid phase of the reaction medium is maintained in the range of from about 300 to about 6,000 parts per million by weight (ppmw), in the range of from about 700 to about 4,200 ppmw, or in the range of from 1,200 to 3,000 ppmw. When bromine is present in the catalyst system, the fluid-phase feed stream can comprise bromine in an amount such that the concentration of bromine in the liquid phase of the reaction medium is maintained in the range of from about 300 to about 5,000 ppmw, in the range of from about 600 to about 4,000 ppmw, or in the range of from 900 to 3,000 ppmw. When manganese is present in the catalyst system, the fluid-phase feed stream can comprise manganese in an amount such that the concentration of manganese in the liquid phase of the reaction medium is maintained in the range of from about 20 to about 1,000 ppmw, in the range of from about 40 to about 500 ppmw, or in the range of from 50 to 200 ppmw.

In one embodiment of the present invention, cobalt and bromine can both be present in the catalyst system. The weight ratio of cobalt to bromine (Co:Br) in the catalyst system can be in the range of from about 0.25:1 to about 4:1, in the range of from about 0.5:1 to about 3:1, or in the range of from 0.75:1 to 2:1. In another embodiment, cobalt and manganese can both be present in the catalyst system. The weight ratio of cobalt to manganese (Co:Mn) in the catalyst system can be in the range of from about 0.3:1 to about 40:1, in the range of from about 5:1 to about 30:1, or in the range of from 10:1 to 25:1.

During oxidation, the oxidizable compound (e.g., para-xylene) can be continuously introduced into oxidation zone 10 at a rate of at least about 5,000 kilograms per hour, at a rate in the range of from about 10,000 to about 80,000 kilograms per hour, or in the range of from 20,000 to 50,000 kilograms per hour. During oxidation, the ratio of the mass flow rate of the solvent to the mass flow rate of the oxidizable compound entering oxidation zone 10 can be maintained in the range of from about 2:1 to about 50:1, in the range of from about 5:1 to about 40:1, or in the range of from 7.5:1 to 25:1.

The predominately gas-phase oxidant stream introduced into oxidation zone 10 can comprise in the range of from about 5 to about 40 mole percent molecular oxygen, in the range of from about 15 to about 30 mole percent molecular oxygen, or in the range of from 18 to 24 mole percent molecular oxygen. The balance of the oxidant stream can be comprised primarily of a gas or gases, such as nitrogen, that are inert to oxidation. In one embodiment, the oxidant stream consists essentially of molecular oxygen and nitrogen. In another embodiment, the oxidant stream can be dry air that comprises about 21 mole percent molecular oxygen and about 78 to about 81 mole percent nitrogen. In an alternative embodiment of the present invention, the oxidant stream can comprise substantially pure oxygen.

During liquid-phase oxidation in oxidation zone 10, the oxidant stream can be introduced into oxidation zone 10 in an amount that provides molecular oxygen somewhat exceeding the stoichiometric oxygen demand. Thus, the ratio of the mass flow rate of the oxidant stream (e.g., air) to the mass flow rate of the oxidizable compound (e.g., para-xylene) entering oxidation zone 10 can be maintained in the range of from about 0.5:1 to about 20:1, in the range of from about 1:1 to about 10:1, or in the range of from 2:1 to 6:1.

The liquid-phase oxidation reaction carried out in oxidation zone 10 can be a precipitating reaction that generates solids. In one embodiment, the liquid-phase oxidation carried out in oxidation zone 10 can cause at least about 10 weight percent of the oxidizable compound (e.g., para-xylene) introduced into oxidation zone 10 to form solids (e.g., crude terephthalic acid (CTA) particles) in the reaction medium. In another embodiment, the liquid-phase oxidation carried out in oxidation zone 10 can cause at least about 50 weight percent of the oxidizable compound (e.g., para-xylene) introduced into oxidation zone 10 to form solids (e.g., CTA particles) in the reaction medium. In yet another embodiment, the liquid-phase oxidation carried out in oxidation zone 10 can cause at least about 90 weight percent of the oxidizable compound (e.g., para-xylene) introduced into oxidation zone 10 to form solids (e.g., CTA particles) in the reaction medium. In one embodiment, the solids content of the reaction medium can be maintained in the range of from about 5 to about 40 weight percent, in the range of from about 10 to about 35 weight percent, or in the range of from 15 to 30 weight percent. As used herein, the term "solids content" shall denote the weight percent solids in a multi-phase mixture.

During oxidation in oxidation zone 10, the multi-phase reaction medium can be maintained at an elevated temperature in the range of from about 125 to about 200° C., in the range of from about 150 to about 180° C., or in the range of from 155 to 165° C. The overhead pressure in oxidation zone 10 can be maintained in the range of from about 1 to about 20 bar gauge (barg), in the range of from about 2 to about 12 barg, or in the range of from 4 to 8 barg.

In the embodiment of FIG. 1, a crude slurry can be withdrawn from an outlet of oxidation zone 10 via line 12. The solid phase of the crude slurry in line 12 can be formed primarily of solid particles of CTA. The liquid phase of the crude slurry in line 12 can be a liquid mother liquor comprising at least a portion of the solvent, one or more catalyst components, and minor amounts of dissolved terephthalic acid (TPA). The solids content of the crude slurry in line 12 can be the same as the solids content of the reaction medium in oxidation zone 10, discussed above.

In one embodiment of the present invention, the crude slurry in line 12 can comprise impurities. As used herein, the term "impurities" is defined as any substance other than TPA, solvent, catalyst, and water. Such impurities can include oxidation byproducts formed during the at least partial oxidation of the above-mentioned oxidizable compound (e.g., para-xylene) including, but not limited to, benzoic acid (BA), bromo-benzoic acid, bromo-acetic acid, isophthalic acid, trimellitic acid, 2,5,4'-tricarboxybiphenyl, 2,5,4'-tricarboxybenzophenone, para-toluic acid (p-TAc), 4-carboxybenzaldehyde (4-CBA), monocarboxyfluorenones, monocarboxyfluorenes, and/or dicarboxyfluorenones.

Subsequent to removal from oxidation zone 10, the crude slurry can optionally be introduced into purification zone 14 via line 12. In one embodiment, the crude slurry can be treated in purification zone 14 such that the concentration of at least one of the above-mentioned impurities in the crude slurry is reduced, thereby producing a purified slurry. Such reduction in the concentration of impurities in the TPA can be accomplished by oxidative digestion, hydrogenation, and/or dissolution/recrystallization.

In one embodiment of the present invention, the crude slurry fed to purification zone 14 can have a 4-CBA content of at least about 100 parts per million based on the weight of the solids in the crude slurry ($ppmw_{cs}$), in the range of from about 200 to about 10,000 $ppmw_{cs}$, or in the range of from 800 to 5,000 $ppmw_{cs}$. The crude slurry fed to purification zone 14 can have a p-TAc content of at least about 250 $ppmw_{cs}$, in the range of from about 300 to about 5,000 $ppmw_{cs}$, or in the range of from 400 to 1,500 $ppmw_{cs}$. The purified slurry exiting purification zone 14 can have a 4-CBA content of less than about 150 parts per million based on the weight of the solids in the purified slurry ($ppmw_{ps}$), less than about 100 $ppmw_{ps}$, or less than 50 $ppmw_{ps}$. The purified slurry exiting purification zone 14 can have a p-TAc content of less than about 300 $ppmw_{ps}$, less than about 200 $ppmw_{ps}$, or less than 150 $ppmw_{ps}$. In one embodiment, treatment of the crude slurry in purification zone 14 can cause the purified slurry exiting purification zone 14 to have a 4-CBA and/or p-TAc content that is at least about 50 percent less than the 4-CBA and/or p-TAc content of the crude slurry fed to purification zone 14, at least about 85 percent less, or at least 95 percent less. By way of illustration, if the 4-CBA content of the crude slurry fed to purification zone 14 is 200 $ppmw_{cs}$ and the 4-CBA content of the purified slurry exiting purification zone 14 is 100 $ppmw_{ps}$, then the 4-CBA content of the purified slurry is 50 percent less than the 4-CBA content of the crude slurry.

In one embodiment of the present invention, the crude slurry can be subjected to purification by oxidative digestion in purification zone 14. As used herein, the term "oxidative digestion" denotes a process step or steps where a feed comprising solid particles is subjected to oxidation under conditions sufficient to permit oxidation of at least a portion of the impurities originally trapped in the solid particles. Purification zone 14 can comprise one or more reactors or zones. In one embodiment, purification zone 14 can comprise one or more mechanically-agitated reactors. A secondary oxidant stream, which can have the same composition as the gas-phase oxidant stream fed to oxidation zone 10 discussed above, can be introduced into purification zone 14 to provide the molecular oxygen required for oxidative digestion. Additional oxidation catalyst can be added if necessary. In an alternative embodiment of the present invention, a stream comprising hydrogen can be introduced into purification zone 14 for hydrogenation of the crude slurry.

When oxidative digestion is employed in purification zone 14, the temperature at which oxidative digestion is carried out can be at least about 10° C. greater than the temperature of oxidation in oxidation zone 10, in the range of from about 20 to about 80° C. greater, or in the range of from 30 to 50° C. greater. The additional heat required for the operation of purification zone 14 can be provided by supplying a vaporized solvent to purification zone 14 and allowing the vaporized solvent to condense therein. The oxidative digestion temperature in purification zone 14 can be maintained in the range of from about 180 to about 240° C., in the range of from about 190 to about 220° C., or in the range of from 200 to 210° C. The oxidative digestion pressure in purification zone 14 can be maintained in the range of from about 100 to about 350 pounds per square inch gauge (psig), in the range of from about 175 to about 275 psig, or in the range of from 185 to 225 psig.

In one embodiment of the present invention, purification zone 14 can include two digestion reactors/zones—an initial digester and a final digester. When purification zone 14 includes an initial digester and a final digester, the final digester can be operated at a lower temperature and pressure than the initial digester. In one embodiment, the operating temperature of the final digester can be at least about 2° C. lower than the operating temperature of the initial digester, or in the range of from about 5 to about 15° C. lower than the operating temperature of the initial digester. In one embodiment, the operating pressure of the final digester can be at least about 5 psig lower than the operating pressure of the initial digester, or in the range of from about 10 to about 50 psig lower than the operating pressure of the initial digester. The operating temperature of the initial digester can be in the range of from about 195 to about 225° C., in the range of from 205 to 215° C., or about 210° C. The operating pressure of the initial digester can be in the range of from about 215 to about 235 psig, or about 225 psig. The operating temperature of the final digester can be in the range of from about 190 to about 220° C., in the range of from 200 to 210° C., or about 205° C. The operating pressure of the final digester can be in the range of from about 190 to 210 psig, or about 200 psig.

In one embodiment of the present invention, purification zone 14 can comprise optional first and second solvent swap zones. Optional first and second solvent swap zones can operate to replace at least a portion of the existing solvent in a slurry with a replacement solvent. Equipment suitable for such replacement includes, but is not limited to, a decanter centrifuge followed by a reslurry with replacement solvent, a disc stack centrifuge, an advancing front crystallizer, or multiple decanter centrifuges with optional counter current washing. The replacement oxidation solvent can have substantially the same composition as the solvent introduced into oxidation zone 10, as described above.

In one embodiment, the crude slurry fed to purification zone 14 can be treated in the optional first solvent swap zone prior to purification of the crude slurry by the above-mentioned oxidative digestion. In another embodiment, a purified slurry resulting from oxidative digestion of the crude slurry can be treated in the optional second solvent swap zone.

Optionally, at least a portion of the displaced oxidation solvent from the optional first and/or second solvent swap zones can be discharged from purification zone 14. In one embodiment, at least a portion of the displaced oxidation solvent can be routed to oxidation zone 10.

In another embodiment of the present invention, purification zone 14 can comprise an optional crystallization zone and/or an optional cooling zone. A purified slurry resulting from the above-mentioned oxidative digestion of the crude slurry can be treated in the optional crystallization zone to at least partially increase the particle size distribution of the purified slurry. Optional crystallization zone can comprise any equipment known in the art that can operate to increase the particle size distribution of the purified slurry. When an optional cooling zone is employed, the purified slurry can be cooled therein to a temperature in the range of from about 20 to about 195° C. When both a crystallization zone and a cooling zone are employed, the purified slurry can be treated first in the crystallization zone and subsequently in the cooling zone.

Referring again to FIG. 1, a purified slurry can be withdrawn from an outlet of purification zone 14 via line 16. The solid phase of the purified slurry can be formed primarily of purified terephthalic acid (PTA) particles, while the liquid phase can be formed of a mother liquor. The solids content of the purified slurry in line 16 can be in the range of from about 5 to about 40 weight percent, in the range of from about 10 to about 35 weight percent, or in the range of from 15 to 30 weight percent. The purified slurry in line 16 can be introduced into product isolation zone 18 for at least partial recovery of the solid PTA particles.

Optionally, at least a portion of the crude slurry in line 12 can be introduced into product isolation zone 18 via line 12a. As mentioned above, the solid phase of the crude slurry can be formed primarily of CTA particles, while the liquid phase can be formed of a mother liquor. The solids content of the crude slurry in line 12a can be in the range of from about 5 to about 40 weight percent, in the range of from about 10 to about 35 weight percent, or in the range of from 15 to 30 weight percent. The crude slurry in line 12a can be introduced into product isolation zone 18 for recovery of the solid CTA particles.

Product isolation zone 18 can separate the crude slurry and/or the purified slurry into a predominately fluid phase mother liquor and a wet cake. Product isolation zone 18 can comprise any method of solid/liquid separation known in the art that is capable of generating a wet cake and a mother liquor stream. In addition, it may be desirable for product isolation zone 18 to have the capability of washing the wet cake. Suitable equipment for use in product isolation zone 18 includes, but is not limited to, a pressure drum filter, a vacuum filter, a vacuum drum filter, a vacuum belt filter, multiple solid bowl centrifuges with optional counter current wash, or a perforated centrifuge.

In one embodiment of the present invention, a wash stream can be introduced into product isolation zone 18 to wash at least a portion of the wet cake generated in product isolation zone 18, thereby producing a washed wet cake. In one embodiment, the wash stream can comprise acetic acid and/or water. Optionally, after washing the wet cake, the used wash liquor can be withdrawn from product isolation zone 18, and at least a portion of the wash liquor can be routed, either directly or indirectly, to oxidation zone 10.

The above-mentioned wet cake generated in product isolation zone 18 can be discharged via line 20. In one embodiment of the present invention, the wet cake generated in product isolation zone 18 can primarily comprise solid particles of carboxylic acid. In one embodiment, the carboxylic acid can be an aromatic dicarboxylic acid, which can be solid TPA particles. The solid TPA particles can comprise CTA and/or PTA particles. In one embodiment, the solid particles can have a mean particle size in the range of from about 1 to about 500 µm, in the range of from about 10 to about 350 µm, or in the range of from 20 to 200 µm.

In one embodiment of the present invention, the wet cake can comprise in the range of from about 2 to about 25 weight percent liquid, in the range of from about 4 to about 20 weight percent liquid, or in the range of from 6 to 15 weight percent liquid. Additionally, the wet cake in line 20 can comprise oxidation byproducts, as discussed above. Furthermore, the wet cake in line 20 can comprise acetic acid and/or water.

In one embodiment of the present invention, the wet cake in line 20 can be introduced into drying zone 100 via line 20. The wet cake in line 20 can be fed to drying zone 100 at a rate of at least about 20 pounds per hour per square foot (lbs/hr/ft$^2$) of the inner surface area of drying zone 100. In another embodiment, the wet cake in line 20 can be fed to drying zone 100 at a feed rate of at least about 35 lbs/hr/ft$^2$, or in the range of from about 40 to about 175 lbs/hr/ft$^2$. The wet cake in line 20 can have an inlet temperature in the range of from about 0 to about 220° C., in the range of from about 20 to about 200° C., in the range of from about 40 to about 150° C., in the range of from about 60 to about 120° C., or in the range of from 65 to 105° C. upon entering drying zone 100. As used herein, the term "inlet temperature" is defined as the temperature of the wet cake immediately upon being introduced into drying zone 100.

Drying zone 100 can operate to produce a substantially dry TPA particulate product comprising solid TPA particles. As used herein, the term "substantially dry" is defined as a product comprising less than about 2 weight percent liquid. In another embodiment of the present invention, the substantially dry TPA particulate product can comprise less than about 1 weight percent liquid, less than about 0.5 weight percent liquid, less than about 0.2 weight percent liquid, or less than 0.1 weight percent liquid.

In one embodiment, at least a portion of the vapor produced from the liquid removed from the solid TPA particles can be removed from drying zone 100 via line 22. The vapor in line 22 can comprise solvent as described above in relation to the solvent contained in the fluid-phase feed stream fed to oxidation zone 10 (e.g., acetic acid and/or water).

Referring still to FIG. 1, in one embodiment of the present invention, vacuum source 24 can be used to create vacuum conditions in drying zone 100. During drying operations, drying zone 100 can be operated at a pressure in the range of from about 50 to about 750 torr, in the range of from about 100 to about 700 torr, or in the range of from 150 to 650 torr. In another embodiment, vacuum source 24 can also operate to create vacuum conditions in product isolation zone 18, such that product isolation zone 18 and drying zone 100 share vacuum source 24. In another embodiment, a condenser (not depicted) can be disposed substantially between drying zone 100 and vacuum source 24. The condenser can operate to condense at least a portion of the vapor in line 22.

In one embodiment of the present invention, the solid particles can have an average residence time in drying zone 100 of less than about 7 minutes, less than about 5 minutes, less than about 3 minutes, less than about 2 minutes, or less than 1 minute. As used herein, the term "residence time" is defined as the difference in time between the introduction of a solid particle into drying zone 100 via line 20 and the time when that same solid particle exits the drying zone via line 26.

In another embodiment of the present invention, the solid particles have a measurable exit temperature upon being withdrawn from drying zone 100 via line 26. In one embodiment, the solid particles can have an exit temperature of less than about 250° C., in the range of form about 105 to about 240° C., in the range of from about 110 to about 200° C., in the range of from about 115 to about 175° C., or in the range of from 120 to 160° C. As used herein, the term "exit temperature" is defined as the temperature of the solid particles immediately upon exiting drying zone 100 (e.g., upon introduction into line, 26). Additionally, the exit temperature of the solid particles can be at least about 25° C. greater, at least about 50° C. greater, or at least 100° C. greater than the inlet temperature of the wet cake as discussed above.

In one embodiment of the present invention, the solid particles exiting drying zone 100 via line 26 can pass through vacuum seal 28. Vacuum seal 28 can operate to allow solid particles to be withdrawn from drying zone 100 while at least partially maintaining the pressure in drying zone 100. In one embodiment, vacuum seal 28 can maintain the pressure in drying zone 100 such that, upon withdrawal of solid particles, the pressure change in drying zone 100 is less than about 20 percent, less than about 10 percent, or less than 5 percent. Vacuum seal 28 can be any vacuum seal device that can at least partially maintain the pressure in drying zone 100 while allowing the withdrawal of solids. An example of a suitable device that can be used for vacuum seal 28 includes, but is not limited to, a rotary air lock valve.

In one embodiment of the present invention, drying zone 100 can comprise an inert atmosphere during drying operations. As used herein, the term "inert atmosphere" is defined as an atmosphere that is substantially non-reactive in the processes of the present invention. Such an inert atmosphere can be achieved by introducing an inert gas into drying zone 100. Any method known in the art for introducing a gas into a vessel can be employed to introduce the inert gas into drying zone 100. In one embodiment, introduction of the inert gas can be achieved by allowing the gas to leak through vacuum seal 28 into line 26, and subsequently into drying zone 100. In an alternate embodiment, the inert gas can be directly supplied to drying zone 100 through an inert gas inlet (not depicted). The inert gas can be fed to drying zone 100 at a feed rate of less than about 5 standard cubic feet of gas per pound of wet cake in drying zone 100 (SCF/lb), less than about 3 SCF/lb, or less than 1 SCF/lb. Suitable examples of inert gases useful in the present invention include, but are not limited to, nitrogen and/or air.

In one embodiment of the present invention, drying zone 100 can be defined within a dryer. In another embodiment, drying zone 100 can be defined within a contact dryer. As used herein, the term "contact dryer" is defined as a dryer where heat is transferred to the material being dried (e.g., solid TPA particles) by physically contacting the material being dried with a thermally conductive wall (e.g., a heated inner surface) that separates a heat source (e.g., a heat transfer medium) from the material being dried. In an alternate embodiment, drying zone 100 can be defined within a plurality of contact dryers arranged in series.

FIG. 2 illustrates one embodiment of a contact dryer 102 that can define drying zone 100. In this embodiment, dryer 102 can comprise a substantially horizontally disposed elongated tubular cylinder 104 presenting an inner surface 106. Furthermore, dryer 102 can comprise a jacket 108 which allows a heat transfer medium to circulate therethrough. Additionally, dryer 102 can comprise feed inlet 110, product outlet 112, and vapor outlet 118. Optionally, a drying gas inlet 120 can also be provided.

In one embodiment of the present invention, cylinder 104 can have a length of less than about 80 feet, less than about 40 feet, or less than 20 feet. Additionally, cylinder 104 can have an inner diameter in the range of from about 1 to about 15 feet. Inner surface 106 can have an area in the range of from about 4 to about 40 square feet ($ft^2$), in the range of from about 6 to about 35 $ft^2$, or in the range of from 8 to 30 $ft^2$.

In one embodiment of the present invention, jacket 108 can substantially envelop cylinder 104, thereby allowing a heat transfer medium to circulate between the outer surface of cylinder 104 and the inner surface of jacket 108. During drying operations, the heat transfer medium circulating in jacket 108 can operate to transfer heat to cylinder 104. This transfer of heat can raise the temperature of inner surface 106, resulting in a heated inner surface. During drying operations, inner surface 106 can have a temperature of at least about 100° C., in the range of from about 115 to about 265° C., or in the range of from 200 to 250° C. During drying operations, jacket 108 can have a temperature in the range of from about 120 to about 280° C., in the range of from about 160 to about 250° C., or in the range of from 200 to 240° C.

Jacket 108 can comprise heat transfer medium inlet 114 and heat transfer medium outlet 116. Heat transfer medium inlet 114 allows for the introduction of the heat transfer medium into jacket 108, and spent heat transfer medium can be withdrawn via heat transfer medium outlet 116.

The heat transfer medium employed in the present invention can be any medium sufficient to increase the temperature of inner surface 106 as discussed above. In one embodiment, the heat transfer medium can be a liquid and/or a gas. Suitable examples of heat transfer mediums useful in the present invention include, but are not limited to, steam, water, oil, and/or commercially available natural or synthetic heat transfer medium fluids. The heat transfer medium introduced into jacket 108 can have an inlet temperature in the range of from about 120 to about 280° C., in the range of from about 160 to about 250° C., or in the range of from 200 to 240° C. As used herein, when referring to the heat transfer medium, the term "inlet temperature" is defined as being the temperature of the heat transfer medium immediately upon being introduced into jacket 108. Furthermore, the heat transfer medium can have an outlet temperature in the range of from about 110 to about 270° C., in the range of from about 130 to about 250° C., or in the range of from 150 to 240° C. Additionally, the pressure in jacket 108 during drying operations can be maintained in the range of from about 50 to about 700 pounds per square inch gauge (psig), in the range of from about 70 to about 650 psig, or in the range of from 90 to 600 psig.

Referring still to FIG. 2, dryer 102 can comprise a paddle rotor 122. Paddle rotor 122 can be disposed substantially coaxially within cylinder 104. Paddle rotor 122 can comprise a plurality of radial arms 124. Radial arms 124 can be positioned along the length of paddle rotor 122 in a substantially helical pattern. Each of radial arms 124 can comprise a paddle or blade 126 rotatably attached to the end of radial arms 124. Paddles 126 can be adjustably secured to the end of radial arms 124 so as to permit presetting of the pitch of each paddle 126.

FIG. 3 illustrates in detail radial arms 124 and paddles 126. The length of radial arms 124 combined with paddles 126 can extend at least about 80 percent, at least about 85 percent, or at least 90 percent of the distance of the annular space created between paddle rotor 122's outer surface 128 and inner surface 106.

Referring again to FIG. 2, at least a portion of the wet cake comprising the solid particles as discussed above can be introduced into dryer 102 via feed inlet 110. Paddle rotor 122 can be operable to facilitate contact of the solid particles with inner surface 106 and to facilitate movement of the solid particles through cylinder 104. To achieve such contacting and movement, paddle rotor 122 can rotate so as to impart centrifugal and axially forward forces on at least a portion of the solid particles. In one embodiment, the centrifugal force created by paddle rotor 122 can be sufficient to at least partially overcome the force of gravity, thereby forming a thin layer of the solid particles over at least a portion of inner surface 106. In one embodiment, at least about 10 percent, at least about 40 percent, or at least 70 percent of the solid particles introduced into dryer 102 can form a thin layer over at least a portion of inner surface 106. The centrifugal force created by paddle rotor 122 can be sufficient to form a thin layer of solid particles over at least about 20 percent, at least about 35 percent, or at least 50 percent of inner surface 106. The thin layer of solid particles created on inner surface 106 can have an average thickness of less than about 1.5 inches, less than about 1 inch, or less than 0.5 inches.

The axially forward forces created by paddle rotor 122 can be sufficient to transport the solid particles from feed inlet 110 to product outlet 112 within the residence times discussed above. Arms 124 and paddles 126 can be oriented so that when paddle rotor 122 rotates, the solid particles follow a substantially helical path from feed inlet 110, along inner surface 106, to product outlet 112. One example of a substantially helical path the solid particles could follow during drying operations is depicted by path 130.

In order to achieve the above-mentioned centrifugal and axially forward forces on the solid particles, paddle rotor 122 can rotate at a sufficient speed. The speed of rotation of paddle rotor 122 can be measured by determining the speed at which the tips of paddles 126 are traveling (tip speed) during drying operations. The tip speed of paddles 126 during drying operations can be at least about 10 cm/s, in the range of from about 20 to about 400 cm/s, in the range of from about 50 to about 300 cm/s, or in the range of from 100 to 150 cm/s.

At least a portion of the liquid removed from the above-mentioned wet cake during drying operations can be discharged via vapor outlet 118. Vapor discharged from vapor outlet 118 can be treated in substantially the same manner as the vapor in line 22 of FIG. 1, discussed above. Vapor outlet 118 can have a diameter that is sufficiently narrow so as to at least partially prevent entrained solids from escaping dryer 102 concurrent with removed vapor. In one embodiment, vapor outlet 118 can have a diameter of less than about 15 feet, less than about 10 feet, or less than 5 feet.

In one embodiment of the present invention, a drying gas may be employed to facilitate at least partial direct-contact drying of the solid particles in dryer 102. When a drying gas is employed, the drying gas can enter dryer 102 via drying gas inlet 120. The drying gas employed in the present invention can be any gas capable of removing at least a portion of the liquid from the above-mentioned wet cake. Suitable examples of drying gases useful in the present invention include, but are not limited to, nitrogen, TPA process off-gases, oxygen-depleted gas, carbon dioxide, carbon monoxide, and/or air. As used herein, the term "TPA process off-gas" is defined as a gas which was used in the oxidation step of a TPA production process. Optionally, the TPA process off-gas can be scrubbed and/or treated in a regenerative thermal oxidation unit prior to being employed as a drying gas. As used herein, the term "oxygen-depleted gas" is defined as a gas having less than about 7 mol percent oxygen. In one embodiment, the oxygen-depleted gas can have an oxygen content of less than about 5 mol percent, less than about 3 mol percent, or less than 1 mol percent.

In one embodiment, the drying gas can have an inlet temperature of at least about the boiling point of the liquid to be removed from the wet cake. In another embodiment, the drying gas can have an inlet temperature in the range of from about 100 to about 250° C., in the range of from about 120 to about 225° C., or in the range of from 140 to 200° C. As used herein, when referring to the drying gas, the term "inlet temperature" is defined as being the temperature of the drying gas immediately upon being introduced into dryer 102. When a drying gas is employed in dryer 102, the pressure in dryer 102 can be up to about 1000 torr during drying operations. The pressure in dryer 102 is determined by measuring the pressure at product outlet 112.

As mentioned above, the solid particles can exit dryer 102 via product outlet 112. In one embodiment of the present invention, the above-mentioned substantially dry TPA particulate product can comprise at least a portion of the solid particles exiting dryer 102 via product outlet 112. In another embodiment, the solid particles exiting dryer 102 via product outlet 112 can be treated in substantially the same manner as the solid particles in line 26 of FIG. 1, discussed above.

In one embodiment of the present invention, dryer 102 can be a thin layer contact dryer. As used herein, the term "thin layer contact dryer" is defined as a contact dryer wherein at least a portion of the solid particles entering the dryer form a layer having an average thickness of less than about 1.5 inches over at least a portion of the heated inner surface of the dryer. Suitable examples of commercially available thin layer contact dryers for use in the present invention include, but are not limited to, a SOLIDAIRE dryer (manufactured by Bepex International LLC, Minneapolis, Minn., USA), or a TURBO-DRYER (manufactured by VOMM S.P.A., Milan, Italy).

It will be understood by one skilled in the art that each of the above-described embodiments, as well as any sub-parts of those embodiments, may be operated in a continuous or a non-continuous manner. Non-continuous operations include, but are not limited to, batch-wise operations, cyclical operations, and/or intermittent operations.

EXAMPLES

The following examples are intended to be illustrative of the present invention in order to teach one of ordinary skill in the art to make and use the invention and are not intended to limit the scope of the invention in any way.

Example 1

Preparation of PTA Wet Cake

Two batches of PTA wet cake were prepared for use in the examples below. Each batch was prepared by mixing glacial acetic acid with dry PTA powder in a 16 cubic foot ribbon mixer. Batch 1 was prepared by first adding approximately 600 lbs of dry PTA powder to the ribbon mixer and turning on the agitator. Next, approximately 67 lbs of glacial acetic acid was added over approximately a 1 hour time period. The mixer was then allowed to operate for several hours to ensure a substantially homogeneous mixture. Bach 2 was prepared in the same manner as batch 1, except approximately 150 lbs of glacial acetic acid was mixed with the 600 lbs of dry PTA powder. After mixing, each batch was analyzed to determine its moisture content. Batch 1 contained 11 weight percent moisture and batch 2 contained 18 weight percent moisture.

Example 2

Dryers

Two different classes of dryers were compared in the examples below for their efficacy in drying a PTA-containing wet cake. The first class of dryer used in the examples below was represented by the TORUSDISC TD 12-4 dryer (manufactured by Bepex International LLC, Minneapolis, Minn., USA). The TORUSDISC TD 12-4 dryer is an indirect heat exchanger having a heated dryer area of 27.6 square feet. The TORUSDISC TD 12-4 represents a class of dryers characterized by a single or twin shaft heated rotor, a heated jacket, and slow, gentle movement of solids through the dryer during drying. Other dryers in this class include the DISCO-THERM-B dryer (manufactured by LIST USA Inc., Charlotte, N.C., USA), the HOLO-FLITE dryer (manufactured by Metso Minerals, Helsinki, Finland), the PORCUPINE processor (manufactured by Bethlehem Corp., Easton, Pa., USA), the K-S NARA PADDLE dryer (manufactured by Komline-Sanderson Engineering Corp., Peapack, N.J., USA), and the ROVACTOR dryer (manufactured by Buss-SMS-Canzler GmbH, Butzbach, Germany).

The second class of dryer used in the examples below was represented by the SOLIDAIRE dryer (manufactured by Bepex International LLC, Minneapolis, Minn., USA). Two different models of the SOLIDAIRE dryer were used in the examples below: the SOLIDAIRE SJS 10-6 and the SOLIDAIRE SJS 8-4. The SOLIDAIRE dryers represent a class of dryers known as thin layer contact dryers, which are characterized by a heated jacket, a heated inner surface, and a paddle rotor having blades that can be angled, shaped, or oriented so as to impart centrifugal and axially forward forces to the material being dried. The SOLIDAIRE dryers are capable of producing a highly agitated thin layer of cake. Each of the SOLIDAIRE dryers employed can be direct and/or indirect heat exchangers. The SJS 10-6 dryer has a heated drying area of 15 square feet, and the SJS 8-4 has a heated drying area of 8 square feet. Another dryer in this class is the TURBO-DRYER (manufactured by VOMM S.P.A., Milan, Italy).

Example 3

Dryer Residence Time

To compare the performance of the dryers described in Example 2, a total of 4 samples of the PTA wet cake containing 18 weight percent moisture, as prepared in Example 1, were dried in a TORUSDISC TD 12-4 dryer and a SOLIDAIRE SJS 10-6 dryer, two samples in each dryer. In each of the 4 runs, the wet cake was metered into the dryer with a screw feeder. The feed rate was varied from 27 pounds per hour per square foot of heated drying area (lbs/hr/ft$^2$) to 93 lbs/hr/ft$^2$. A vacuum system was employed during the drying procedure which removed the acid vapor from the dryer. Additionally, during the drying procedure the dryer was purged with nitrogen. After drying, the dried PTA was removed from the dryers via a rotary air lock valve, which allowed the dry powder to be removed from the dryer while maintaining a substantially constant level of pressure in the dryer. The dry PTA temperature, the moisture content, and the residence time of the dried PTA product were then measured. In each of the 4 runs, the jacket temperature of the dryer was maintained at 180° C. during drying. The results are listed in Table 1, below.

TABLE 1

Effect of Dryer on Residence Time

| | TORUSDISC TD 12-4 | | SOLIDAIRE SJS 10-6 | |
|---|---|---|---|---|
| | Run 1 | Run 2 | Run 3 | Run 4 |
| Wet Cake Feed Rate (lbs/hr/ft$^2$) | 27 | 33 | 40 | 93 |
| Dry PTA Temperature (° C.) | 168 | 160 | 160 | 131 |
| Dry PTA Weight Percent Moisture | 0.05 | 0.09 | 0.03 | 0.01 |
| Dryer Residence Time (min.) | 7.8 | 6.5 | 2.7 | 1.7 |

As can be seen by looking at the results listed in Table 1, each of the two dryers was able to produce a dry PTA product having less than 0.1 weight percent moisture. However, it is clear that the SOLIDAIRE dryer provides shorter residence times than the TORUSDISC dryer, while achieving the same or better level of reduction in moisture.

Example 4

Jacket Temperature and Feed Rate

The effect of the jacket temperature and feed rate on dry PTA temperature, dry PTA weight percent moisture, and dryer residence time was determined by performing drying operations on five samples of the PTA wet cake containing 11 weight percent moisture, as prepared in Example 1. For this determination, a SOLIDAIRE SJS 8-4 dryer was employed. Each sample in turn was metered to the dryer using a screw feeder. The feed rate for each of the five runs was varied from 75 lbs/hr/ft$^2$ to 175 lbs/hr/ft$^2$. Additionally, the jacket temperature of the dryer was varied from 200° C. (Runs 1-3) to 223° C. (Run 4) and 244° C. (Run 5). After drying, the dried PTA was removed from the dryer via a rotary air lock valve, which allowed the dry powder to be removed from the dryer while maintaining a substantially constant level of pressure in the dryer. The dry PTA temperature, the moisture content, and the residence time of the dried PTA product were then measured. The results are listed in Table 2, below.

TABLE 2

Effect of Jacket Temperature and Feed Rate

| | Dryer Jacket Temperature | | | | |
|---|---|---|---|---|---|
| | 200° C. | | | 223° C. | 244° C. |
| | Run 1 | Run 2 | Run 3 | Run 4 | Run 5 |
| Wet Cake Feed Rate (lbs/hr/ft$^2$) | 75 | 113 | 150 | 125 | 175 |
| Dry PTA Temperature (° C.) | 152 | 146 | 117 | 154 | 140 |
| Dry PTA Weight Percent Moisture | 0.11 | 0.03 | 1.1 | 0.09 | 0.05 |
| Dryer Residence Time (min.) | 1.6 | 1.1 | 0.8 | 1.0 | 0.7 |

As can be seen by looking at the results listed in Table 2, the feed rate in Run 3 was increased to 150 lbs/hr/ft$^2$ while maintaining a jacket temperature of 200° C. This resulted in a dried PTA product having an unacceptably high level of moisture content (1.1 weight percent). However, as Runs 4 and 5 demonstrate, when the dryer jacket temperature is increased, the wet cake feed rate can also be increased without having a deleterious effect on the moisture content of the dried PTA product.

Example 5

Thermal Stability of Terephthalic Acid

The thermal stability of terephthalic acid (TPA) was determined by performing thermal gravimetric analysis (TGA) on two samples of crude terephthalic acid (CTA) and two samples of PTA. One of the PTA samples and one of the CTA samples was tested in an air environment, while the other two samples were tested in a nitrogen environment. A modified version of ASTM method E1131-03 (Standard Test Method for Compositional Analysis by Thermogravimetry) was followed for this example. The method was modified by lowering the highest testing temperature to 350° C. The analyses were performed on a HI-RES TGA 2950 THERMOGRAVIMETRIC ANALYZER (manufactured by TA Instruments, New Castle, Del., USA). The scan rate employed in each analysis was 5° C. per minute.

The results from the TGA analysis of TPA are shown in FIGS. 4 and 4a. FIG. 4 depicts the thermal degradation and/or sublimation of terephthalic acid over a temperature range starting at 0° C. and ending at 350° C., while FIG. 4a is a magnified view of FIG. 4, depicting the thermal degradation and/or sublimation of TPA over a temperature range from 185° C. to 285° C. As can be seen by looking at FIG. 4a, it is apparent that severe thermal degradation and/or sublimation of the TPA begins to occur at temperatures greater than about 250° C. Thermal degradation begins to occur at about 250° C. whether the sample is CTA or PTA, and occurs in both air environments and nitrogen environments.

Numerical Ranges

The present description uses numerical ranges to quantify certain parameters relating to the invention. It should be understood that when numerical ranges are provided, such ranges are to be construed as providing literal support for claim limitations that only recite the lower value of the range as well as claims limitation that only recite the upper value of the range. For example, a disclosed numerical range of 10 to 100 provides literal support for a claim reciting "greater than 10" (with no upper bounds) and a claim reciting "less than 100" (with no lower bounds).

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. For example, if the specification describes a specific temperature of 62° F., such a description provides literal support for a broad numerical range of 25° F. to 99° F. (62° F.+/−37° F.), an intermediate numerical range of 43° F. to 81° F. (62° F.+/−19° F.), and a narrow numerical range of 53° F. to 71° F. (62° F.+/−9° F.). These broad, intermediate, and narrow numerical ranges should be applied not only to the specific values, but should also be applied to differences between these specific values. Thus, if the specification describes a first pressure of 110 psia and a second pressure of 48 psia (a difference of 62 psi), the broad, intermediate, and narrow ranges for the pressure difference between these two streams would be 25 to 99 psi, 43 to 81 psi, and 53 to 71 psi, respectively.

Definitions

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "including," "includes," and "include" have the same open-ended meaning as "comprising," "comprises," and "comprise."

As used herein, the terms "having," "has," and "have" have the same open-ended meaning as "comprising," "comprises," and "comprise."

As used herein, the terms "containing," "contains," and "contain" have the same open-ended meaning as "comprising," "comprises," and "comprise."

As used herein, the terms "a," "an," "the," and "said" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

Claims Not Limited to Disclosed Embodiments

The forms of the invention described above are to be used as illustration only, and should not be used in a limiting sense to interpret the scope of the present invention. Obvious modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. A method for drying solid particles comprising an aromatic dicarboxylic acid and a liquid, comprising:
   (a) introducing a wet cake comprising the solid aromatic dicarboxylic acid particles and at least one liquid into a thin layer contact dryer comprising a heated inner surface and a paddle rotor which imparts centrifugal and axially forward force to the wet cake;
   (b) forming a layer of wet cake of at least 10% of the solid particles having an average thickness of less than 1.5 inches over at least a portion of the heated inner surface and
   (c) removing the liquid from the solid particles of the aromatic dicarboxylic acid to thereby produce substantially dry aromatic dicarboxylic acid particles,
   wherein
   the at least one liquid comprises at least one of water and acetic acid,
   the wet cake comprises from about 2 to about 25 weight percent liquid,
   a feed rate of the wet cake to the thin layer contact dryer is at least about 20 lbs/hour per square foot of heated surface area of the thin layer contact dryer,
   an average residence time of the solid particles in the thin layer contact dryer is less than about 7 minutes,
   a temperature of the particles in the thin layer contact dryer does not exceed a temperature of sublimation or thermal degradation according to thermogravimetric analysis of the aromatic dicarboxylic acid,
   an exit temperature of the solid particles from the thin layer contact dryer is less than about 250° C. and
   the dry solid aromatic dicarboxylic acid particles comprise less than about 1 weight percent of the liquid.

2. The method of claim 1, wherein the average residence time is less than about 5 minutes.

3. The method of claim 1, wherein at least about 40 percent of the solid particles form a layer over at least a portion of the inner surface, wherein the layer is less than about 1 inch thick.

4. The method of claim 1, wherein the exit temperature is from about 105 to about 240° C.

5. The method of claim 1, wherein a feed rate of the wet cake to the thin layer contact dryer is from about 40 to about 175 lbs/hour per square foot of heated surface area of the thin layer contact dryer.

6. The method of claim 1, wherein a temperature of the wet cake is from about 20 to 120° C. immediately prior to entering the thin layer contact dryer.

7. The method of claim 1, wherein the substantially dry aromatic dicarboxylic acid particles comprise less than about 0.5 weight percent liquid.

8. The method of claim 1, wherein the aromatic dicarboxylic acid is terephthalic acid.

9. The method of claim 8, wherein the terephthalic acid is crude terephthalic acid.

10. The method of claim 1, wherein the thin layer contact dryer comprises a jacketed cylinder providing the heated inner surface.

11. The method of claim 10, wherein a temperature of the heated inner surface is maintained from about 120 to about 280° C.

12. The method of claim 10, wherein the thin layer contact dryer further comprises a paddle rotor disposed substantially coaxially within the jacketed cylinder.

13. The method of claim 12, wherein the paddle rotor comprises a plurality of radial arms extending from the rotor.

14. The method of claim 13, wherein each of the radial arms comprises a paddle that is rotatable relative to the radial arms.

15. The method of claim 13, wherein the arms and the paddles extend at least about 80 percent of a distance of an annular space between the outer surface of the paddle rotor and the heated inner surface.

16. The method of claim 13, wherein the radial arms form a substantially helical pattern along a length of the paddle rotor.

17. The method of claim 10, wherein the jacket allows for a heat transfer medium to be circulated there through, wherein the heat transfer medium comprises a fluid.

18. The method of claim 17, wherein the jacket comprises a heat transfer medium inlet for introducing the heat transfer medium into the jacket, wherein the heat transfer medium has an inlet temperature of from about 120 to about 280° C.

19. The method of claim 12, wherein the paddle rotor facilitates both contact of the solid particles with the heated inner surface and movement of the solid particles through the jacketed cylinder.

20. The method of claim 19, wherein a layer of the solid particles forms over at least about 20 percent of the heated inner surface.

21. The method of claim 14, wherein the tips of the paddles travel at a speed of at least about 10 cm/s.

22. The method of claim 10, wherein a temperature of the heated surface is from about 115 to about 265° C.

23. The method of claim 1, further comprising introducing a drying gas into the thin layer contact dryer, wherein an inlet temperature of the drying gas is at least about 100° C.

24. The method of claim 1, wherein the thin layer contact dryer comprises an inert atmosphere.

25. The method of claim 1, wherein the thin layer contact dryer further comprises a vacuum seal device through which the solid aromatic dicarboxylic acid particles exit the dryer.

26. The method of claim 25, wherein the vacuum seal device comprises a rotary air lock valve.

27. A method for producing a substantially dry crude terephthalic acid (CTA) particulate product, comprising:
   (a) oxidizing an aromatic compound in an oxidation zone to thereby produce a slurry comprising solid CTA particles;
   (b) treating at least a portion of the slurry in a product isolation zone to thereby produce a wet cake comprising solid CTA particles; and
   (c) drying the wet cake in a thin layer contact dryer comprising a heated inner surface to thereby produce the substantially dry CTA particulate product,
   wherein
   the at least one liquid comprises at least one of water and acetic acid,
   the wet cake comprises from about 2 to about 25 weight percent liquid, a feed rate of the wet cake to the thin layer contact dryer is at least about 20 lbs/hour per square foot of heated surface area of the thin layer contact dryer, at least about 10 percent of the solid CTA particles form a layer having an average thickness of less than about 1.5 inches over at least a portion of the inner surface, an average residence time of the CTA particles in the thin layer contact dryer is less than about 7 minutes, an exit temperature of the solid CTA particles is less than about 250° C., and the dry solid CTA particles comprise less than about 1 weight percent of the liquid.

28. The method of claim 27, wherein the average residence time is less than about 5 minutes.

29. The method of claim 27, wherein the substantially dry CTA particulate product comprises less than about 2 weight percent liquid.

30. The method of claim 27, wherein the exit temperature is from about 105 to about 240° C.

31. The method of claim 27, further comprising creating a vacuum in the product isolation zone and the drying zone during the drying with a common vacuum source.

32. The method of claim 27, wherein the thin layer contact dryer comprises:
a jacketed cylinder providing the heated inner surface, and
a paddle rotor disposed substantially coaxially within the jacketed cylinder.

33. The method of claim 32, wherein the paddle rotor comprises a plurality of radial arms extending from the rotor, wherein each of the radial arms comprises a paddle that is rotatable relative to the radial arms.

34. The method of claim 32, wherein the jacket comprises a heat transfer medium inlet for introducing a heat transfer medium into the jacket, wherein an inlet temperature of the heat transfer medium is from about 120 to about 280° C.

35. The method of claim 32, wherein the paddle rotor facilitates both contact of the solid CTA particles with the heated inner surface and movement of the solid particles through the jacketed cylinder.

36. A method for producing a substantially dry purified terephthalic acid (PTA) particulate product, comprising:
(a) oxidizing an aromatic compound in an oxidation zone to thereby produce a first slurry comprising solid crude terephthalic acid (CTA) particles;
(b) subjecting at least a portion of the CTA particles to purification in a purification zone to thereby produce a second slurry comprising solid PTA particles;
(c) treating at least a portion of the second slurry in a product isolation zone to thereby produce a wet cake comprising the PTA particles; and
(d) drying the wet cake in a thin layer contact dryer to thereby produce the substantially dry PTA particulate product,
wherein
the wet cake comprises from about 2 to about 25 weight percent liquid,
the liquid comprises at least one of water and acetic acid,
a feed rate of the wet cake to the thin layer contact dryer is at least about 20 lbs/hour per square foot of heated surface area of the thin layer contact dryer,
at least about 10 percent of the solid PTA particles form a layer having an average thickness of less than about 1.5 inches over at least a portion of the inner surface, an average residence time of the PTA particles in the thin layer contact dryer is less than about 7 minutes, and
an exit temperature of the solid PTA particles is less than about 250° C. and the dry solid PTA particles comprise less than about 1 weight percent of the liquid.

37. The method of claim 36, wherein the average residence time is less than about 5 minutes.

38. The method of claim 36, wherein the substantially dry PTA particles comprise less than about 1 weight percent liquids.

39. The method of claim 36, wherein the exit temperature is from about 105 to about 240° C.

40. The method of claim 36, further comprising creating a vacuum in the product isolation zone and the drying zone during the drying with a common vacuum source.

41. The method of claim 36, wherein the thin layer contact dryer comprises:
a jacketed cylinder providing the heated inner surface, and
a paddle rotor disposed substantially coaxially within the jacketed cylinder.

42. The method of claim 41, wherein the jacket comprises a heat transfer medium inlet for introducing a heat transfer medium into the jacket, wherein an inlet temperature of the heat transfer medium is from about 120 to about 280° C.

43. The method of claim 41 wherein the paddle rotor comprises a plurality of radial arms extending from the rotor, wherein each of the radial arms comprises a paddle that is rotatable relative to the radial arms.

44. The method of claim 41, wherein the paddle rotor facilitates both contact of the solid particles with the heated inner surface and movement of the solid particles through the jacketed cylinder.

45. A method for drying a wet cake comprising terephthalic acid (TPA), comprising:
(a) introducing the wet cake into a thin layer contact dryer; and
(b) drying the wet cake in said dryer to thereby produce a dry TPA product,
wherein
the wet cake comprises from about 2 to about 25 weight percent liquid,
the liquid comprises at least one of water and acetic acid,
a feed rate of the wet cake to the thin layer contact dryer is at least about 20 lbs/hour per square foot of heated surface area of the thin layer contact dryer,
at least a portion of the TPA in the wet cake forms a thin layer on the inside surface of the dryer, and
a temperature of the dry TPA exiting from the dryer is from about 105 to about 240° C., and
the dry solid TPA particles comprise less than about 1 weight percent of the liquid.

46. The method of claim 45, wherein an average residence time of the TPA in the thin layer contact dryer is less than about 7 minutes.

47. The method of claim 45, wherein a temperature of the dry TPA product exiting the thin layer dryer is from about 125 to about 200° C.

48. The method of claim 45, wherein the dry TPA product comprises less than 1 weight percent liquid.

49. The method of claim 45, wherein the thin layer contact dryer comprises a jacketed cylinder having a heated inner surface.

50. The method of claim 49, wherein a feed rate of the wet cake to the thin layer dryer is at least about 35 lbs/hour per square foot of the heated inner surface.

51. The method of claim 49, wherein the thin layer contact dryer further comprises a paddle rotor having a plurality of blades.

52. The method of claim 51, wherein at least a portion of the blades impart centrifugal and axially forward forces on the TPA.

53. The method of claim 49, wherein a temperature of the inner surface of the thin layer contact dryer is from about 120 to about 270° C.

54. A method for drying a wet cake comprising terephthalic acid (TPA), said method comprising:
 (a) introducing the wet cake into a dryer, wherein the dryer comprises a thin layer contact dryer having a heated inner surface and a jacket, wherein the jacket temperature of the dryer is maintained in the range of from about 120 to about 270° C., wherein at least about 10 percent of the solid particles form a layer over at least a portion of the inner surface, wherein the layer has an average thickness of less than about 1.5 inches and wherein the wet cake is fed to the dryer at a feed rate of at least about 35 lbs/hour per square foot of the heated inner surface during the drying; and
 (b) drying the wet cake in the dryer to thereby produce a dry TPA product, wherein said TPA has an average residence time in the dryer of from about 1 minute to about 5 minutes, and wherein the dry TPA product has a temperature in the range of from about 105 to about 240° C. upon exiting the dryer,
wherein
 the wet cake comprises from about 2 to about 25 weight percent liquid,
 the liquid comprises at least one of water and acetic acid, and
 the dry TPA product comprises less than about 1 weight percent of the liquid.

55. The method of claim 54, wherein the TPA has an average residence time in the dryer of from about 1 minute to about 3 minutes.

56. The method of claim 54, wherein the dry TPA product has less than about 0.1 weight percent moisture.

* * * * *